(12) United States Patent
Thompson

(10) Patent No.: US 11,229,549 B2
(45) Date of Patent: Jan. 25, 2022

(54) TEAR TRANSPLANTATION AND MULTI-PART CONTACT LENS WITH ABSORBENT PORTION

(71) Applicant: Vance M. Thompson, Sioux Falls, SD (US)

(72) Inventor: Vance M. Thompson, Sioux Falls, SD (US)

(*) Notice: Subject to any disclaimer, the term of this patent is extended or adjusted under 35 U.S.C. 154(b) by 87 days.

(21) Appl. No.: 16/574,716

(22) Filed: Sep. 18, 2019

(65) Prior Publication Data

US 2021/0077297 A1    Mar. 18, 2021

(51) Int. Cl.
*A61F 9/00*   (2006.01)
*A61K 35/30*  (2015.01)
*A61K 9/00*   (2006.01)

(52) U.S. Cl.
CPC .......... *A61F 9/0017* (2013.01); *A61K 9/0048* (2013.01); *A61K 35/30* (2013.01)

(58) Field of Classification Search
None
See application file for complete search history.

(56) References Cited

U.S. PATENT DOCUMENTS

| | | | |
|---|---|---|---|
| 5,660,085 A | | 8/1997 | Domb |
| 5,830,913 A | * | 11/1998 | Ogawa .................... A61P 27/02 514/569 |
| 8,408,698 B2 | | 4/2013 | Legerton |
| 8,669,241 B2 | * | 3/2014 | Matsumura .......... A61K 9/0048 514/77 |
| 8,864,306 B2 | | 10/2014 | de Juan, Jr. et al. |
| 9,910,296 B2 | | 3/2018 | Harant et al. |
| 10,537,608 B2 | * | 1/2020 | Hsu .......................... C07K 7/06 |
| 2013/0242255 A1 | | 9/2013 | Caldarise et al. |
| 2017/0348344 A1 | * | 12/2017 | Inagaki ................ A61K 9/0048 |

FOREIGN PATENT DOCUMENTS

WO    WO 2015/175250 A1    11/2015
WO    WO 2017/167939 A1    10/2017

* cited by examiner

*Primary Examiner* — Melissa S Mercier

(57) ABSTRACT

A contact lens or conjunctival cover, including an internal absorbent medium; an external carrier medium; the external carrier medium having openings therein that allow fluid to pass between an exterior of the contact lens or conjunctival cover and the internal absorbent medium thereby to be absorbed and released by the internal absorbent medium. Also, a method of treating dry eye syndrome, including: gathering donor tears from eyes of an individual having healthy tears; storing the donor tears in an absorbent medium; placing the absorbent medium with the donor tears absorbed therein in contact with an eye or eyes affected by dry eye syndrome; and dispersing the donor tears over an ocular surface of the eyes affected by dry eye syndrome.

11 Claims, 5 Drawing Sheets

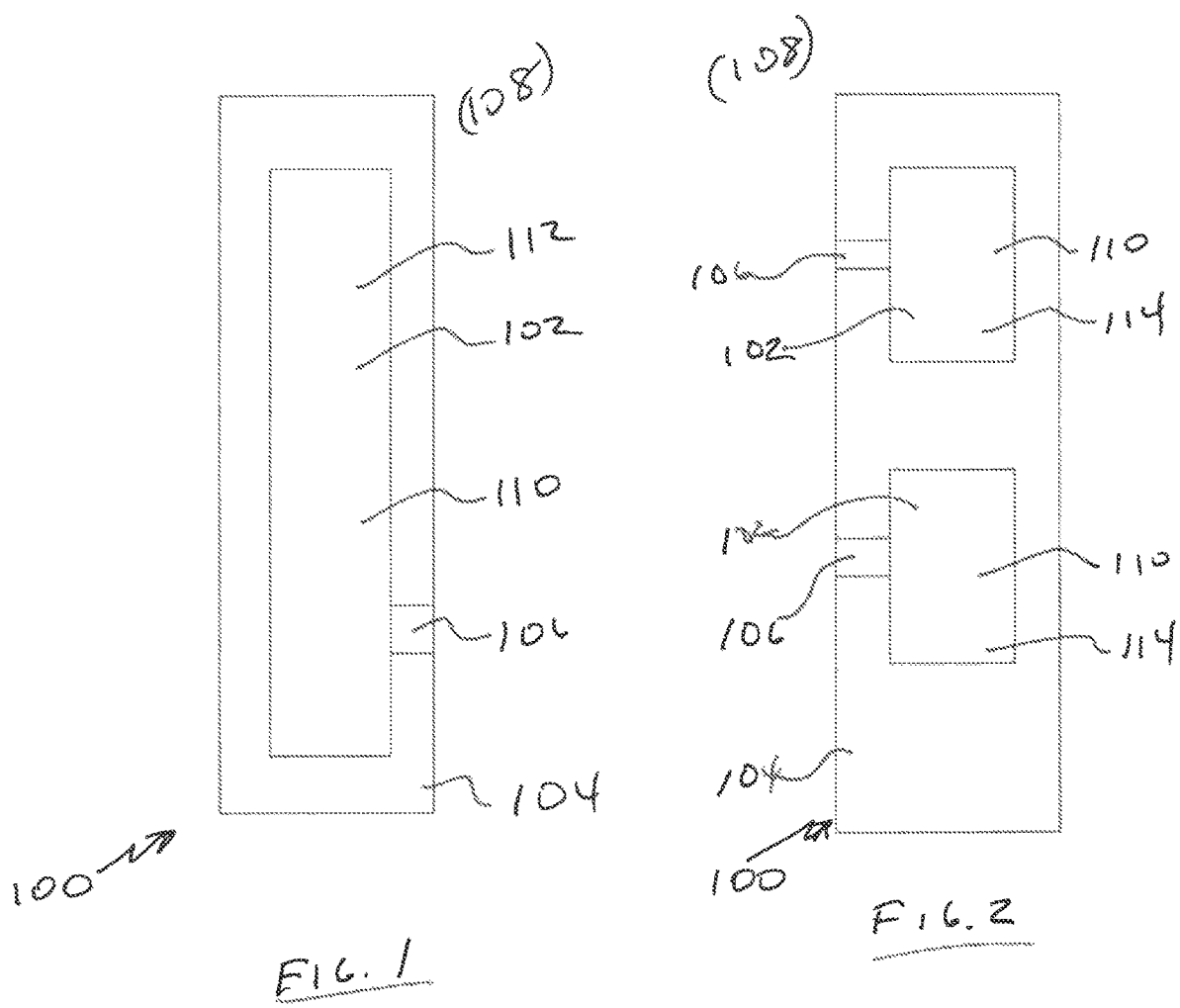

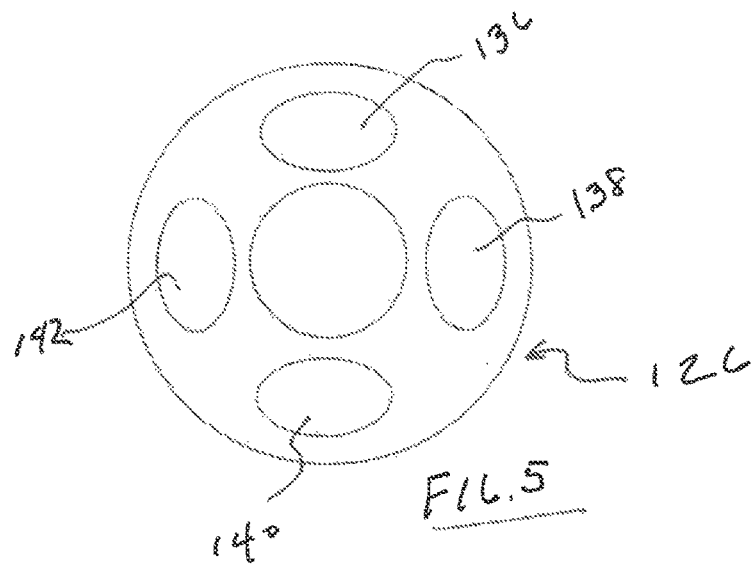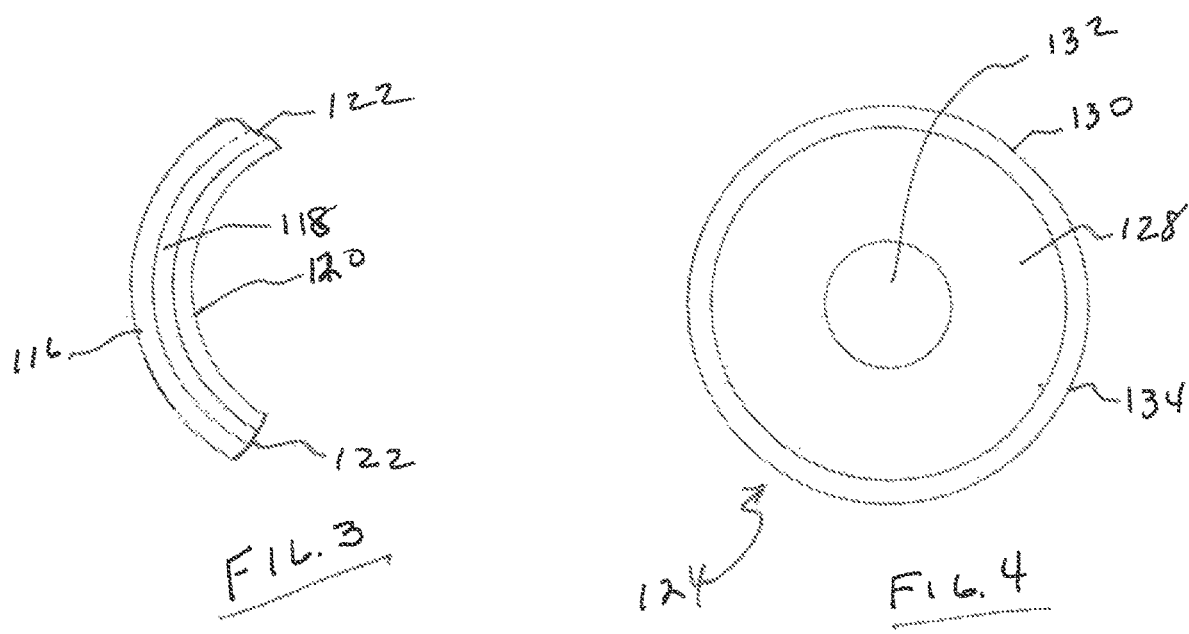

TEAR TRANSPLANTATION AND MULTI-PART CONTACT LENS WITH ABSORBENT PORTION

TECHNICAL FIELD

Embodiments of the invention relate generally to the treatment of dry eye syndrome. More specifically, embodiments of the invention relate to the supplementation of a patient's natural tears.

BACKGROUND

The tear film covers the anterior structures of the eye and is generally considered to be multi-layered in structure. From the corneal surface outward the tear film includes a mucin layer, an aqueous layer and a lipid layer. The mucin layer overlies the surface of the cornea and the conjunctiva and serves to provide an interface between the corneal epithelium and the conjunctival epithelium and the further layers of the tear film. Without the mucin layer the corneal epithelium is generally considered to be hydrophobic because it contains considerable amounts of lipid. Overlying the mucin layer is the aqueous layer consisting largely of water and a small amount of salt and various other trace chemicals. Overlying the aqueous layer is the lipid layer formed of secretions of the meibomian glands and other lipid secreting glands located in and around the eyelids. The tear film protects the tissues of the corneal epithelium from drying and also fills in or bridges minor gaps or irregularities in the corneal epithelium to provide a smooth refractive surface interface between the front of the eye and the ambient atmosphere. Thus, the anterior most refractive interface between the air and the eye is actually formed by the tear film rather than the cornea itself.

The interface between the tear film and the atmosphere represents the most powerful optical focusing interface in the eye. The tear film interface with the atmosphere accounts for approximately two thirds of the focusing power the eye. This focusing power varies but on average is approximately 43 diopters. Because the focusing power at the tear film interface is so large, small changes in the tear film can have a large effect on refraction and clarity of focusing.

When refraction of light occurs in the eye the most powerful focusing element of the eye is generally considered to be the anterior surface of the cornea. In fact, focusing primarily occurs at the interface between the tear film and the atmosphere. Accordingly, the tear film is extremely important for refractive reasons in the eye. In addition, the tear film moistens lubricates and assists in nourishing and carrying away metabolic debris from the cornea.

Generally, the tear film is considered to include a mucin layer nearest to the cornea and an aqueous layer overlying the mucin layer and a lipid layer overlying the aqueous layer. There are many circumstances under which the tear film fails to perform adequately and the cornea may suffer because of the tear film's failure to perform properly. For example, in some circumstances the tear film may have a deficiency of the aqueous layer. In further circumstances the mucin layer or lipid layer of the tear film may be insufficient and the tear film may not perform properly. Various deficiencies are improper functions of the tear film are generally categorized as belonging to dry eyes syndrome. Many systemic diseases and conditions may also contribute to improper functioning of the tear film.

Dry eye syndrome is one of the most commonly treated eye problems in the United States. Dry eye syndrome is also known as keratitis sicca, keratoconjunctivitis sicca (KCS) xerophthalmia, and lacrimal insufficiency. It is estimated that over ten million Americans and 30 million persons worldwide suffer from dry eye syndrome.

For a large fraction of dry eye patients, dry eye syndrome creates discomfort or annoyance. For those severely afflicted, dry eye syndrome can be debilitating and, in some circumstances, even sight-threatening. In extremely severe cases, dry eye syndrome can even lead to the loss of an eye.

Dry eye syndrome typically results from deficiency in the quality or quantity of tears produced by the patient. Precorneal tear film has traditionally been considered to have a three-layered structure. The closest to the cornea lies the mucin, or mucus, layer. The mucin layer provides an interface between the corneal epithelium and the remainder of the tear film. Overlying the mucin layer is the watery aqueous layer, which is the thickest layer of the three. The outermost layer of the precorneal tear film is the lipid layer. The lipid layer is an oily film that reduces evaporation from the aqueous layer beneath it.

The middle aqueous layer provides moisture to the corneal tissue, carries important nutrients, and serves to remove metabolic waste produced by the cornea. Deficiency in any of the three layers of the precorneal tear film can result in complaints of dry, gritty feeling or burning eyes.

The mucin that forms the mucin layer, nearest the cornea, is secreted by goblet cells in the conjunctiva. The conjunctiva is the transparent tissue that covers the sclera and the backside of the eyelids. The mucin layer functions to decrease surface tension of the tear film. In addition, the cornea itself is hydrophobic. Without the mucin layer to provide a bridge between the cornea and the aqueous layer, the aqueous layer would bead up and allow dry spot formation on the cornea.

The aqueous layer is secreted primarily by the glands of Wolfring and Krause located in the eyelid margin. The aqueous layer helps provide an optically smooth, transparent surface to the precorneal tear film. The lipid layer is secreted by the meibomian glands, and the glands of Zeiss and Moll. The glands of Zeiss and Moll are also located at the eyelid margin.

Blinking is essential to maintenance of the precorneal tear film. During each blink, the eyelid wipes over the surface of the cornea, smoothing the mucin layer and spreading the overlying aqueous and lipid layers to provide a completely wetted surface. In between blinks, the tear film thins due to evaporation of the aqueous layer. If evaporation is excessive, dry spots may form on the surface of the cornea.

The formation of dry spots that may form on the surface of the cornea is sometimes referred to as tear breakup. One clinical test that is utilized to evaluate tear breakup is measuring of the tear breakup time. This is sometimes abbreviated TBUT. To evaluate tear breakup time fluoroscein or a similar dye is introduced to the tears and the tears are observed typically via a slitlamp biomicroscope. If fluoroscein is used the cornea is illuminated with cobalt blue or ultraviolet light. The patient is then asked to hold their eyes open without blinking for as long as possible and the period of time between the last blink and the appearance of dry spots on the cornea is measured and recorded. A tear breakup time of less than 10 seconds between the last blink and the appearance of the first dry spot on the cornea is considered to be abnormal. Tear breakup typically begins at one or several foci on the surface of the cornea and will spread from those foci to form larger dry areas within a short period of time.

Deficiency, or imperfect quality, of any of the three component layers can lead to dry eye symptoms. Many systemic and external factors can contribute to dry eye syndrome. For example, Sjogren's syndrome is associated with arthritic diseases in combination with dry eye and dry mouth. Deficiency of Vitamin A, use of oral contraceptives and environmental factors can all contribute to dry eye syndrome.

Recent research into the natural history of dry eye syndrome has shown that the disease progresses through four stages. Each stage is a consequence of the preceding stage. The stages are:
1. Loss of water from the aqueous layer of the tear film leading to an increase in the tear film osmolarity;
2. Loss of conjunctival goblet cells and decreased corneal glycogen;
3. Increased loss of corneal squamous epithelial cells;
4. Destabilization of the interface between the corneal surface and the tear film.

Either decreased secretion of tear film components or increased evaporation lead to increased tear film osmolarity and the following stages that lead to eventual corneal decompensation and the serious consequences of dry eye syndrome.

The adnexa of the eye may also be involved in dry eye syndrome. The adnexa of the eye include the structures surrounding the eye such as the eyelids, eye lashes, the tear drainage and tear production structures. Blepharitis commonly contributes to dry eye syndrome. Blepharitis typically results from bacterial infection of the tiny glands in the margin of the eyelid. These glands include the glands of Zeiss, Moll and Wolfring as well as the meibomian glands. Most commonly, the affected glands are the meibomian glands. In bacterial blepharitis, bacterial infection causes the meibomian glands to become plugged, and thus not be able to produce a normal lipid layer to contribute to the tear film. Some bacteria that infect the glands also secrete exotoxins that seep out of the glands into the eye and injure the corneal epithelium.

Treatments of dry eye syndrome vary depending upon the type of presentation. The most common treatment for dry eye syndrome is the use of artificial tear supplements to provide additional moisture and lubrication to the corneal surface. Artificial tear eye drops are placed on the eye by the patient. Artificial tear supplements must be used regularly and often to be effective.

Lubricant ointments may also be employed. Ointments are usually used at bedtime because they tend to be messy and blur vision. For some patients, even the use of ointments is not sufficient to provide comfort during sleep.

Tears drain from the eye through the lacrimal drainage system. Tiny openings at the nasal corner of each upper and lower eyelid are called the lacrimal puncta. The lacrimal puncta lead into ducts that drain into the nasopharynx.

One treatment for dry eye syndrome is to partially or completely close one or more lacrimal puncta to reduce tear outflow into the lacrimal drainage apparatus. Traditionally, this closure was accomplished surgically or by cautery. In the last decade, however, temporary and permanent punctal occlusion plugs have been utilized.

Permanent punctal plugs are typically made from surgical silicone; temporary plugs are generally made of soluble collagen. Collagen plugs dissolve over a period of days and are helpful in diagnosis.

Punctal plugs are placed into the lacrimal puncta, or lacrimal drainage ducts. The plugs impede the outflow of tears from the eye. This approach slows the outflow of tears and retains them in the eyes longer, often relieving symptoms. Punctal plugs have the distinct advantage of being readily removable and avoid the issues of scar formation.

Blepharitis is sometimes treated by the use of antibiotic medications. Another important treatment for blepharitis is the application of warm soaks and lid scrubs. In this form of treatment, the patient applies a warm wet washcloth to the eyelids for a period of time to provide humidity, warmth and to help soften blockage of and restore flow from the meibomian glands. Lid scrubs are practiced by taking a mild, nonirritating soap and vigorously scrubbing the eyelid margins with their eyes closed, so as to massage the meibomian glands and increase production. The surfactant helps to dissolve the greasy blockage of the meibomian glands.

A variety of researchers have been seeking other medicinal treatments for dry eye syndrome. Largely, this research is directed at pharmaceutical efforts to increase tear production.

Recent research has also indicated that inflammation plays a significant role in the development of dry eye syndrome. One treatment based on this research involves the use of anti-inflammatories applied to the eye to mitigate inflammation.

Despite the many treatment options available, there remains no cure for dry eye syndrome. A great many patients still have substantial and even debilitating discomfort because of dry eye syndrome. Very few treatment options exist to provide comfort for dry eye syndrome patients.

SUMMARY

Embodiments of the invention are expected to solve many of the above problems.

An example embodiment of the invention include a method of treating dry eye syndrome including gathering donor tears from an individual having healthy tears, storing the donor tears in an absorbent medium, placing the absorbent medium with donor tears in contact with the eyes affected by dry eye syndrome and dispersing the donor tears over the ocular surface of the eye affected by dry eye syndrome.

Another example embodiment of the invention includes a structure to be applied to the eye the patient comprising an absorbent material therein adapted to absorb donor tears from an individual having a healthy tear film and to release the donor tears proximate an eye having an insufficient tear film affected by dry eye syndrome.

Another example embodiment of the invention includes a structure in the form of a contact lens having a tear storage reservoir enclosed therein in which donor tears or artificial tears may be stored and from which donor tears may be released onto or into an eye that is affected by dry eye syndrome to supplement naturally produced tears of the eye.

Another example embodiment of the invention includes a contact lens structure having multiple layers. The multiple layers include an absorbent interlayer adapted to receive and store donor tears or artificial tears and also adapted to release the donor tears or artificial tears onto an eye affected by dry eye syndrome. The contact lens according to this example embodiment may have an anterior layer of conventional contact lens material which is either rigid material or hydrophilic material the interior highly absorbent layer and a posterior layer also of conventional contact lens material which is either rigid material or hydrophilic material.

It is noted that hydrophilic contact lens materials are known. Hydrophilic contact lens materials are typically expected to have a water content (by weight) of from approximately 38% to 75%.

For the purposes of this application highly absorbent materials are considered to be those materials that absorb normal saline solution or water (or tears or some similar substances) at a weight percent of higher than 75%. According to another embodiment of the invention the highly absorbent materials are considered to be those that absorb normal saline solution or water at a weight percent higher than 100%. According to another embodiment of the invention, the highly absorbent materials are considered to be those that absorb normal saline solution or water at a weight percent higher than 1000%. For example, superabsorbent polymers may be utilized. Superabsorbent polymers are commonly made from the polymerization of acrylic acid blended with sodium hydroxide in the presence of an initiator to form a polyacrylic acid sodium salt. The polyacrylic acid sodium salt is sometimes referred to as a sodium polyacrylate. A superabsorbent polymer may absorb 300 times its weight when placed in deionized or distilled water. In the context of embodiments the invention is expected that tears because they are not pure water would be absorbed a rate approximately 50 times the weight of the superabsorbent polymer. This is the rate at which normal saline solution is absorbed by superabsorbent polymers and it is known that human tears composition roughly approximates that of normal saline solution.

According to another example embodiment, highly absorbent materials may include cellulose or fiber-based products, for example, cotton material, sponge or fluff pulp. While these materials absorb less water or saline solution by weight they may also release the water or saline solution more readily than superabsorbent polymers.

According to another example embodiment, the invention includes a method of treating dry eye syndrome, including: gathering donor tears from my eyes of an individual having healthy tears; storing the donor tears in an absorbent medium; placing the absorbent medium with the donor tears absorbed therein in contact with an eye or eyes affected by dry eye syndrome; and dispersing the donor tears over and ocular surface of the eyes affected by dry eye syndrome.

According to another example embodiment, the invention includes utilizing a contact lens that includes gathering donor tears.

According to another example embodiment, the invention includes utilizing a contact lens that includes the absorbent to disperse the donor tears.

According to another example embodiment of the invention, the invention includes utilizing a contact lens that includes the absorbent medium to store the donor tears.

According to another example embodiment, the invention includes selecting the absorbent medium to comprise a superabsorbent material.

According to another example embodiment the invention includes selecting the superabsorbent material to absorb tears at a rate of between 40 to 60 times the weight of the absorbent material.

A further example embodiment includes selecting the absorbent medium to be a highly absorbent material.

A further example embodiment includes sterilizing or disinfecting the donor tears following gathering of the donor tears.

According to a further example embodiment the invention includes a contact lens including an internal absorbent medium; an external carrier medium that surrounds the internal absorbent medium and has openings therein that allow tears to pass between an exterior of the contact lens and the internal absorbent medium thereby to be absorbed and released by the internal absorbent medium.

In a further example embodiment the internal absorbent medium further comprises donor tears.

In another example embodiment, the internal absorbent medium comprises a superabsorbent material.

In a further example embodiment, the superabsorbent material absorbs tears at a rate of between 40 and 60 times the weight of the superabsorbent material.

In another example embodiment, the absorbent material comprises a highly absorbent material.

In another example embodiment, the absorbent material further comprises sterilize or disinfected donor tears.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 1 is a schematic cross sectional view of a multipart structure according to an example embodiment of the invention;

FIG. 2 is a schematic cross-sectional view of a multipart structure according to embodiment the invention;

FIG. 3 is a schematic cross-sectional view of a multi-part structure having multiple layers according to an embodiment of the invention;

FIG. 4 is a schematic elevational view of a multipart structure formed as a contact lens according to an example embodiment of the invention;

FIG. 5 is a schematic elevational view of a multi-part structure formed as a conjunctival cover according to an example embodiment of the invention.

Figure 6:
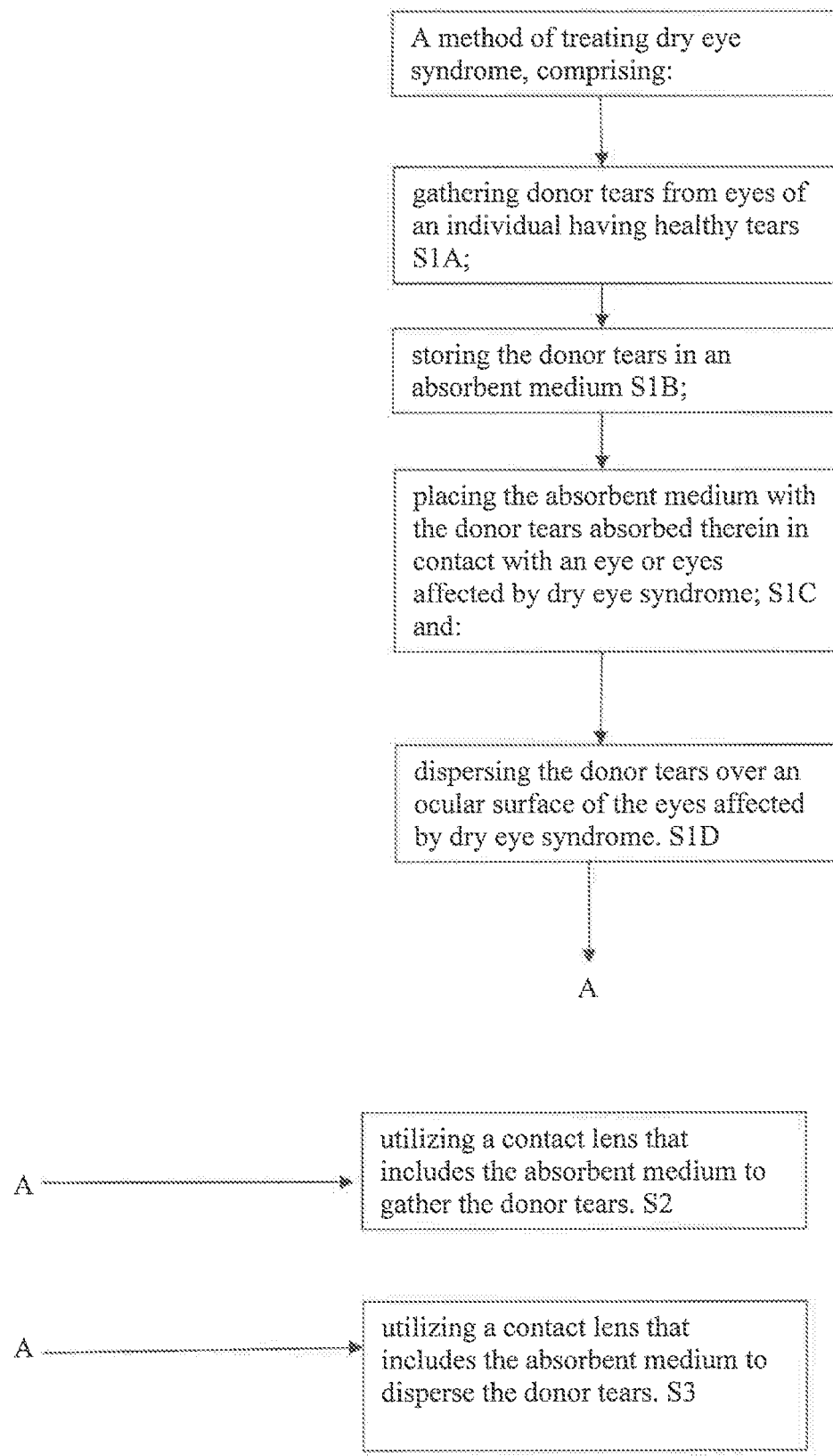
FIG. 6 is a flowchart depicting a method according to an example embodiment of the invention.
Figure 6:
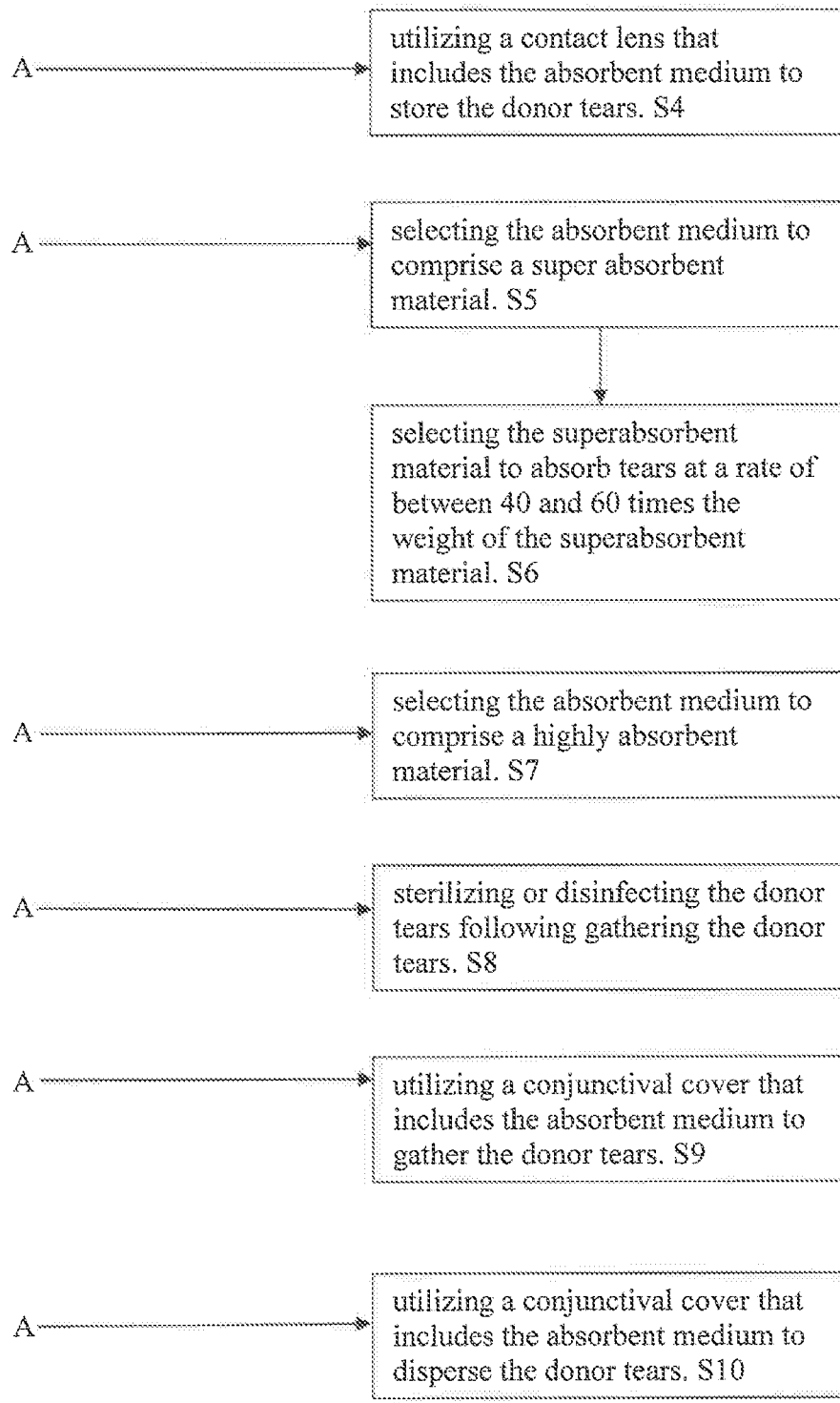
Figure 6:
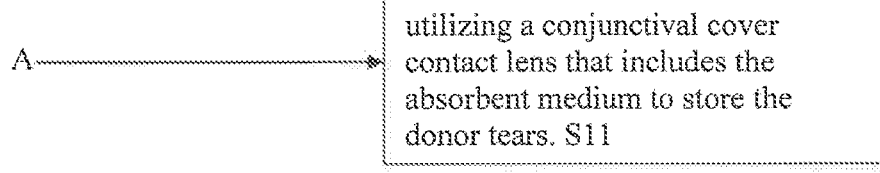

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Referring to FIG. 1, according to an example embodiment schematically depicted, multipart structure 100 to be applied to eye generally includes internal absorbent medium 102, external carrier medium 104, and openings 106 defined in an external carrier medium 104 structure to allow fluid to pass between exterior environment 108 and internal absorbent medium 102. Internal absorbent medium 102 is enclosed in a tear storage reservoir 110. Tear storage reservoir 110 may be a single unitary reservoir 112 or multiple individual reservoirs 114 as depicted in FIG. 2.

Referring to FIG. 3, multipart structure 100 may include multiple layers as schematically depicted. In the depicted example embodiment, the invention includes anterior carrier medium layer 116, center absorbent medium layer 118 and a posterior carrier medium layer 120. According to an example embodiment, center absorbent medium layer 118 is exposed at the outer edges 122 to absorb and release saline solution, water or tears.

According to an example embodiment of the invention, depicted in FIG. 4, multipart structure 100 may take the form of a contact lens 124. According to another example embodiment, depicted in FIG. 5 multipart structure 100 may take the form of a conjunctival cover 126.

Referring to FIG. 4, contact lens 124 generally includes exterior carrier medium 104 and absorbent medium 102. In the depicted embodiment absorbent medium 102 is present in an annular structure 128. In the depicted embodiment of the contact lens 124 includes contact lens body 130 presenting central optical zone 132 and a peripheral edge of 134. Annular structure 128 circumscribes optical zone 132 and extends to proximate peripheral edge 134 in the depicted embodiment. Annular structure 128 is in fluid communication with an exterior of an exterior carrier medium 104 via openings 106 not visible in this depiction.

Referring to FIG. 5, conjunctival cover 126 generally includes annular exterior carrier medium 136 and multiple tear storage reservoirs 110 including absorbent medium 102. The depicted embodiment includes first reservoir 136, second reservoir 138, third reservoir 140 and fourth reservoir 142. The number and configuration of note multiple tear storage reservoir is one time depicted in this embodiment is purely for example. Any number of tear storage reservoirs 110 may be present. In addition, tear storage reservoirs 110 may include a singular tear storage reservoir 110 in an annular shape or any other shape. Each tear storage reservoir should be in fluid communication with an exterior of annular exterior carrier medium 136 or other external carrier medium 104.

Internal absorbent medium 102, for the purposes of this application, may include a highly absorbent material which is considered to be those materials that absorb normal saline solution or water as well as tears or some similar substances at a weight percent higher than 75%. According to another example embodiment of the invention internal absorbent medium 102 may include highly absorbent material which absorbs saline solution, water or tears at a weight percent higher than 100%. According to another example embodiment of the invention, in medium 102 may include highly absorbent materials that absorb normal saline solution or water at a weight percent higher than 1000%.

According to a further example embodiment of the invention, internal absorbent medium 102 may be formed of a super absorbent material that absorbs saline solution, water or tears at a rate of between 40 and 60 times the weight of the superabsorbent material.

According to an example embodiment of the invention, external carrier medium 104 may be formed of soft or rigid contact lens materials. For example, external carrier medium 104 may be formed of a hydrophilic contact lens material having a water content ranging between 10% and 79%. According to another example embodiment the hydrophilic contact lens material may have a water content between 38% and 79%. Such materials include, for example, polyHEMA, Tefilcon, Tetrafilcon, Crofilcon other hydrogels and silicone hydrogel materials as well as any other hydrophilic contact lens material known to those skilled in the art or that should become known to those skilled in the art in the future. The listing of a particular material here should not be considered limiting.

According to another example embodiment, external carrier medium 104 may be formed from an oxygen permeable rigid contact lens material. Rigid contact lens materials may include for example polymers including a combination of polymethylmethacrylate, silicones and fluoropolymer. These materials allow oxygen and other gases to pass directly through the lens to the eye.

According to an example embodiment depicted in FIG. 6, the invention includes a method of treating dry eye syndrome, including gathering donor tears from eyes of an individual having healthy tears S1A; storing the donor tears in an absorbent medium S1B; placing the absorbent medium with the donor tears absorbed therein in contact with an eye or eyes affected by dry eye syndrome S1C; and dispersing the donor tears over an ocular surface of the eyes affected by dry eye syndrome S1D.

According to another example embodiment the method includes utilizing a contact lens that includes the absorbent medium to gather the donor tears S2.

Another example embodiment of the invention includes utilizing a contact lens that includes the absorbent medium to disperse the donor tears S3.

According to a further example embodiment the invention includes utilizing a contact lens that includes the absorbent medium to store the donor tears S4.

In another method according to an example embodiment of the invention, the method includes selecting the absorbent medium to comprise a super absorbent material S5.

A further example embodiment includes selecting the superabsorbent material to absorb tears at a rate of between 40 and 60 times the weight of the superabsorbent material S6.

Another example embodiment includes selecting the absorbent medium to comprise a highly absorbent material S7.

In another example embodiment the method includes sterilizing or disinfecting the donor tears following gathering the donor tears S8.

According to a further example embodiment the method includes utilizing a conjunctival cover that includes the absorbent medium to gather the donor tears S9.

Another example embodiment includes utilizing a conjunctival cover that includes the absorbent medium to disperse the donor tears S10.

And yet a further example embodiment the method includes utilizing a conjunctival cover contact lens that includes the absorbent medium to store the donor tears S11.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of treating dry eye syndrome, comprising:
    gathering donor tears from eyes of an individual having healthy tears;
    storing the donor tears in an absorbent medium;
    placing the absorbent medium with the donor tears absorbed therein in contact with an eye or eyes affected by dry eye syndrome; and
    dispersing the donor tears over an ocular surface of the eyes affected by dry eye syndrome.

2. The method as claimed in claim 1, further comprising utilizing a contact lens that includes the absorbent medium to gather the donor tears.

3. The method as claimed in claim 1, further comprising utilizing a contact lens that includes the absorbent medium to disperse the donor tears.

4. The method as claimed in claim 1, further comprising utilizing a contact lens that includes the absorbent medium to store the donor tears.

5. The method as claimed in claim 1, further comprising selecting the absorbent medium to comprise a super absorbent material.

6. The method as claimed in claim 5, further comprising selecting the superabsorbent material to absorb tears at a rate of between 40 and 60 times the weight of the superabsorbent material.

7. The method as claimed in claim 1, further comprising selecting the absorbent medium to comprise a highly absorbent material.

8. The method as claimed in claim 1, further comprising sterilizing or disinfecting the donor tears following gathering the donor tears.

9. The method as claimed in claim 1, further comprising utilizing a conjunctival cover that includes the absorbent medium to gather the donor tears.

10. The method as claimed in claim 1, further comprising utilizing a conjunctival cover that includes the absorbent medium to disperse the donor tears.

11. The method as claimed in claim 1, further comprising utilizing a conjunctival cover contact lens that includes the absorbent medium to store the donor tears.

* * * * *